United States Patent [19]

Shay, deceased et al.

[11] Plant 4,724

[45] May 26, 1981

[54] APPLE TREE

[75] Inventors: J. Ralph Shay, deceased, late of Corvallis, Oreg., by Robert E. Witters; Edwin B. Williams, Lafayette, Ind.; Daniel F. Dayton, Urbana, Ill.; L. Fredric Hough, Bloomsbury; Catherine H. Bailey, Englishtown, both of N.J.; Frank H. Emerson; Jules Janick, both of West Lafayette, Ind.

[73] Assignee: State of Oregon Acting by and through the State Board of Higher Education on Behalf of Oregon State University, Corvallis, Oreg.

[21] Appl. No.: 131,141

[22] Filed: Mar. 17, 1980

[51] Int. Cl.[3] ..... A0IH5/00

[52] U.S. Cl. ..... Plt./34

[58] Field of Search ..... Plt./34

*Primary Examiner*—Robert E. Bagwill

[57] ABSTRACT

An apple tree having immunity to scab and attractive fruit of high quality as a late summer dessert apple.

3 Drawing Figures

This invention is a new and distinct cultivar of apple tree. It originated as a seedling of known parentage planted in 1963 in the Clark Breeding Orchard, at the Horticulture Farm of the Department of Horticulture at the Purdue University Agricultural Experiment Station, Lafayette, Ind. In this orchard its position in Block A was Row 7, Tree 18, having the designation PRI 1773-8 in the Purdue University breeding records. It was selected by applicants when it first came into fruit in September, 1970, and scions were collected and sent in February, 1971 to the Oregon Agricultural Experiment Station in Corvallis, Oreg. At Corvallis, the scions were grafted into an existing seedling apple tree at the Botany Farm, Range 6 North, Row 1, Tree 15, and the tree produced fruits each year from 1974 through 1979. These activities were conducted in an attempt to develop apple trees with high fruit quality and resistance to *Venturia inaequalis* (cke.) Wint., the casual agent for the apple scab disease.

The present new cultivar is a seedling produced from crossing McIntosh as the seed parent and the seedling PRI 612-4 as the pollen parent in 1962 near Westville, Ind. This new cultivar carries a genetic factor $V_f$ inherited from *Malus floribunda* 821 which causes it to be resistant to infection caused by *Venturia inaequalis.* The presence of this genetic factor has been proven first by controlled innoculation tests in the Purdue greenhouse of the seedling and subsequent immunity against natural infections in the field at Lafayette, Ind., and Corvallis, Oreg. The complete pedigree is shown below:

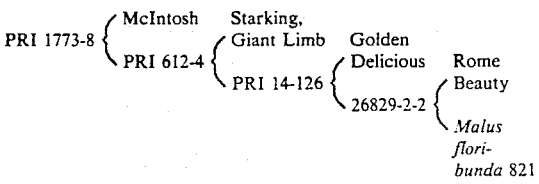

The new cultivar produces a vigorous tree with good annual crops. It is quite tolerant to powdery mildew; in the absence of fungicidal sprays it retains its foliage until late in the season at Corvallis, Oreg., where mildew development is generally severe.

The tree flowers after McIntosh but before Rome Beauty. The apple fruit has good to excellent quality in the Corvallis, Oreg., location. The fruit holds texture and quality for two (2) months or more at 34° F.

The tree has been asexually propagated on seedling and clonal rootstocks. The grafted material has maintained the desired characteristics after propagation.

The accompanying photographs show a typical example of tree form (FIG. 1), blossoms, foliage and fruit (FIGS. 2 and 3) of the new cultivar. The following is a detailed description of the new cultivar with the color description according to the Horticultural Colour Chart, Volumes I and II, by Robert F. Wilson, 1938–41, issued by the British Colour Council in collaboration with the Royal Horticultural Society and published by Henry Stone and Son, Ltd., Banbury, England.

Flower

Pedicel: 2 cm in length.
Corolla: 4 cm in diameter at anthesis.
Color: Spirea Red $025/_1$ (bud) to Phlox Pink $625/_2$ (open flowers).

Fruit

Shape: Round-conic, slightly oblique, regular.
Size: Axial diameter 6.4 cm to 6.7 cm ($2\frac{5}{8}''$ to $2\frac{3}{4}''$); Transverse diameter 6.4 cm to 6.7 cm ($2\frac{5}{8}''$ to $2\frac{3}{4}''$).
Color: Undercolor: Uranium Green, $63/_2$. Overcolor: Currant Red, $821/_1$, covering 80% of the surface.
Skin: Thin, smooth, tender with moderately conspicious white dots, no russetting.
Stem: 2 cm (13/16″), medium thickness, clubbed.
Cavity: Medium depth and width, abrupt angle at shoulder.
Basin: Medium depth and width.
Calyx: Persistent, upright, open.
Calyx tube: Cone-shaped.
Stamens: Median.
Core line: Meeting.
Flesh:
*Texture.*—Fine-grained, tender, juicy.
*Quality.*—Very good, mild sub acid.
*Color.*—Chartreuse Green, $663/_3$.
Maturity season: Two weeks before Jonathan.
Keeping quality: Retains quality and texture 2–3 months at 34° F.

Use: Very good dessert apple grown under climatic conditions of the Willamette Valley, Oreg.

Tree

Form: Upright, vigorous.
Leaves: Ovate, single serrate margin, apex acute, base rounded, length to width ratio = 1.6.

In particular, our new cultivar of apple is distinguished by its field immunity to the apple scab disease, its tolerance to the powdery mildew disease, by its high quality, attractive appearance, and as a late summer dessert apple.

We claim:

1. A new and distinct apple tree substantially as shown and described, particularly characterized by field immunity to apple scab, good fresh fruit quality, smooth waxy attractive skin, and maturity approximately two (2) weeks before Jonathan and three (3) weeks before Delicious.

* * * * *

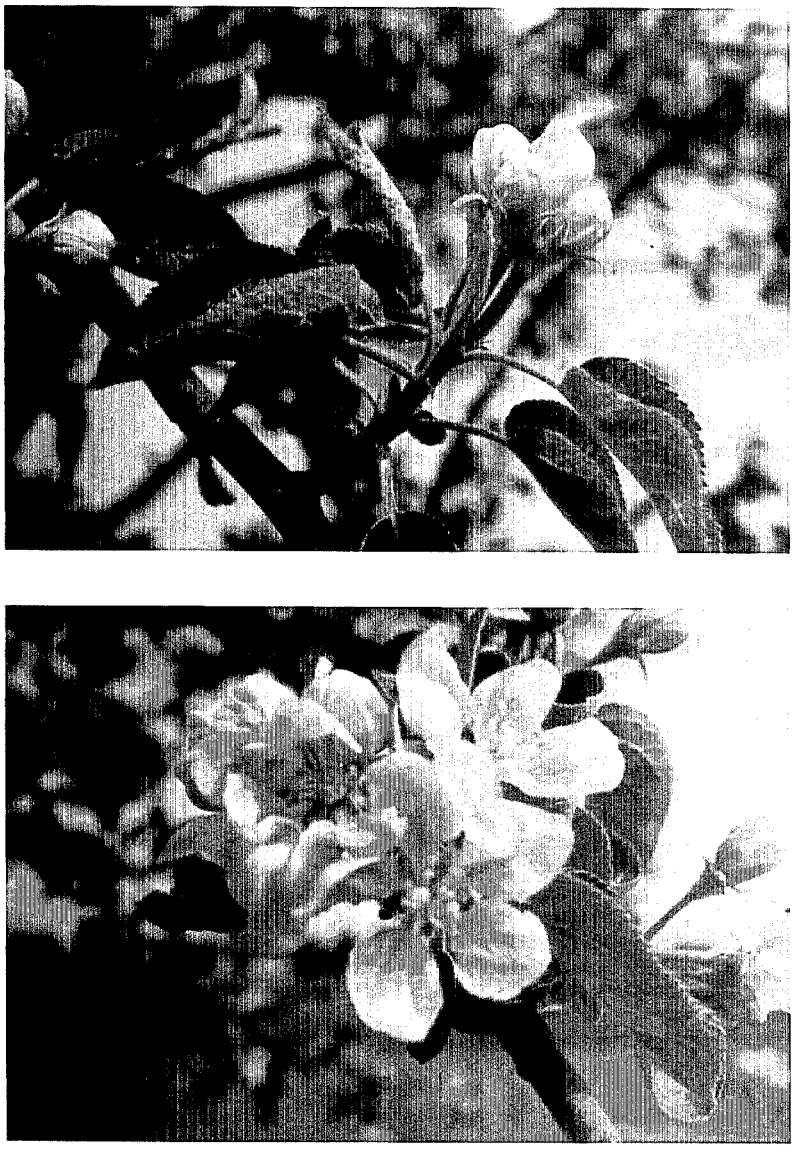
FIG. 2 BLOSSOM AND SPUR LEAVES OF PRI 1773-8 ABOVE: CLUSTER STAGE BELOW: NEARLY FULL BLOOM STAGE

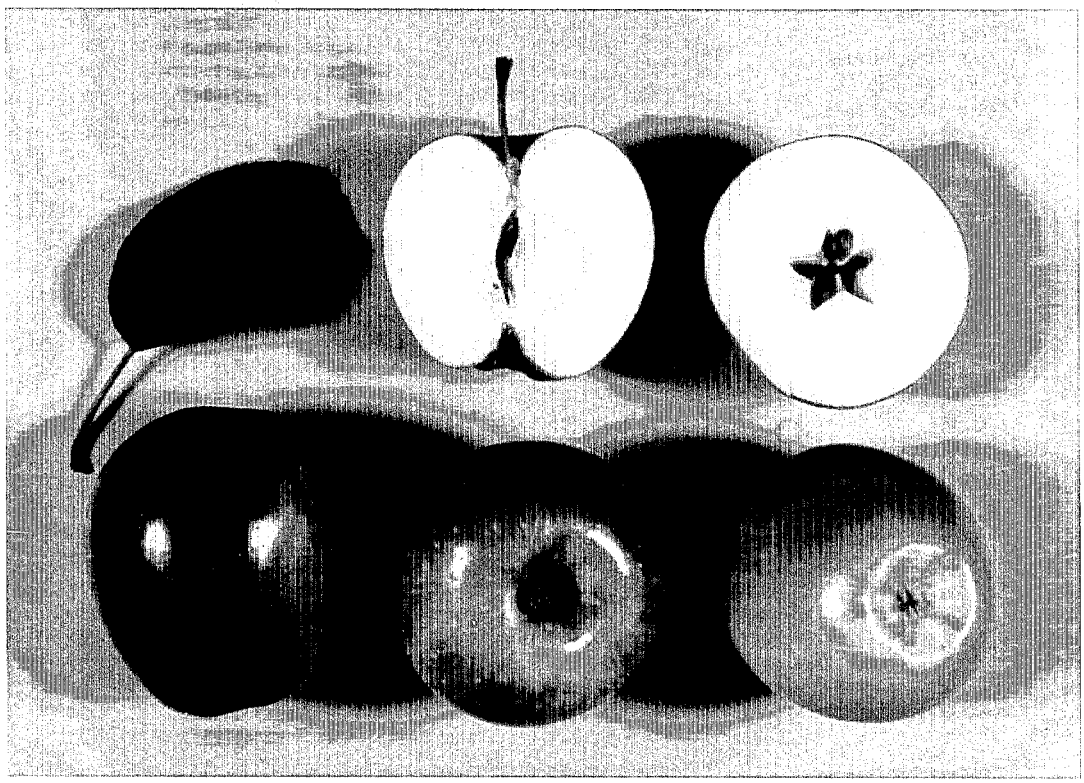
FIG. 3 FRUITS AND LEAF OF PRI 1773-8

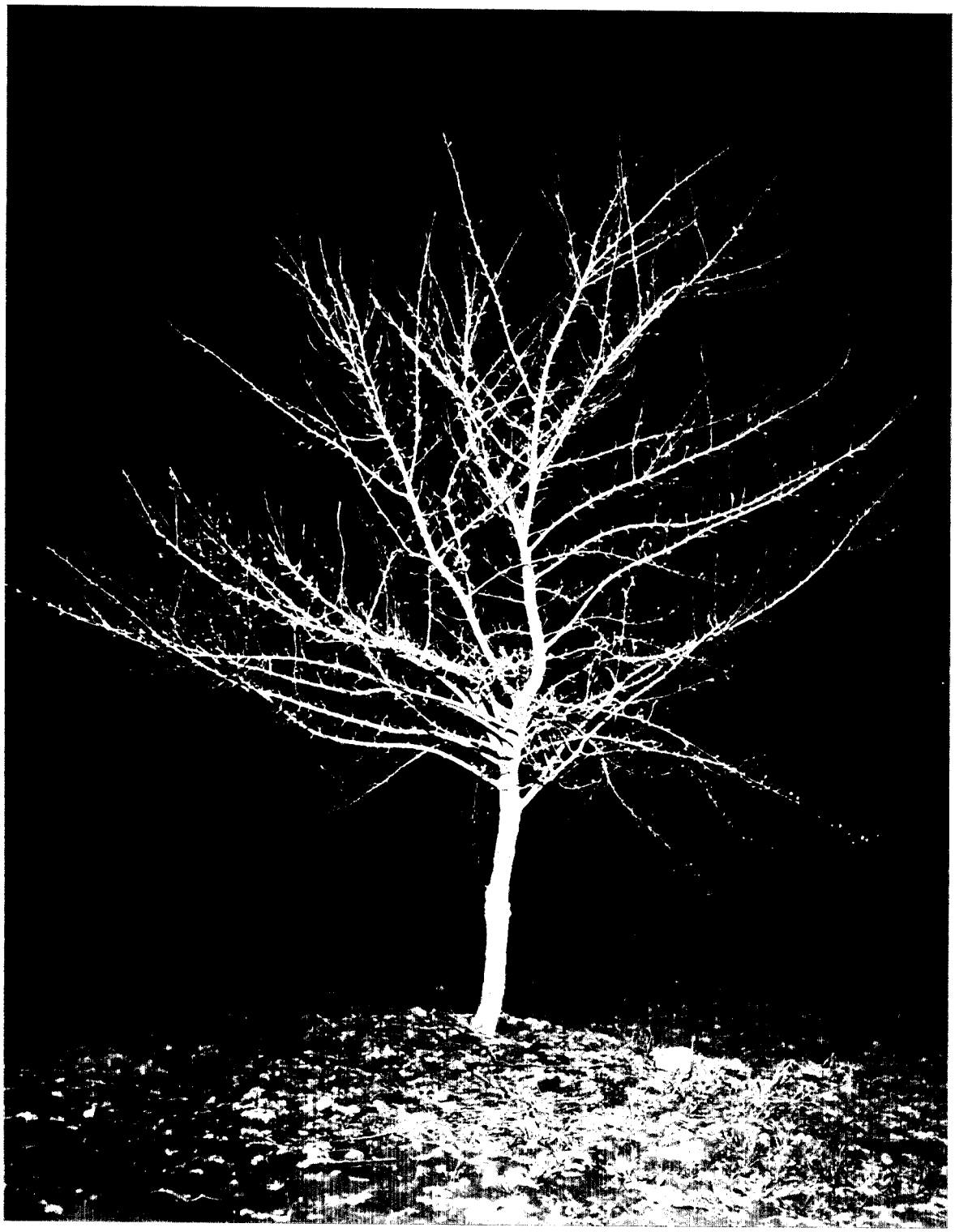
FIG. 1 TREE FORM OF 1773-8